United States Patent
Daggy et al.

(10) Patent No.: US 6,607,749 B1
(45) Date of Patent: Aug. 19, 2003

(54) LIPSTATIN DERIVATIVE-SOLUBLE FIBER TABLETS

(75) Inventors: Bruce P. Daggy, Pine Brook, NJ (US); Kenneth G. Mandel, Parsippany, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/786,518

(22) PCT Filed: Sep. 8, 1999

(86) PCT No.: PCT/US99/20744
§ 371 (c)(1),
(2), (4) Date: Mar. 6, 2001

(87) PCT Pub. No.: WO00/13667
PCT Pub. Date: Mar. 16, 2000

Related U.S. Application Data

(60) Provisional application No. 60/099,399, filed on Sep. 8, 1998.

(51) Int. Cl.[7] .............................. A61K 9/20; A61K 9/22; A61K 9/24; A61K 9/28; A61K 9/36
(52) U.S. Cl. ...................... 424/464; 424/468; 424/472; 424/474; 424/480; 424/482
(58) Field of Search ................................ 424/464, 465, 424/468, 472, 474, 480, 482

(56) References Cited

U.S. PATENT DOCUMENTS

| | | | |
|---|---|---|---|
| 4,017,598 A | * | 4/1977 | Ohno et al. ................... 424/35 |
| 4,189,438 A | | 2/1980 | Umezawa et al. |
| 4,202,824 A | | 5/1980 | Umezawa et al. |
| 5,374,430 A | * | 12/1994 | Newton et al. ............. 424/458 |
| 5,451,409 A | * | 9/1995 | Rencher et al. ............. 424/468 |
| 5,518,730 A | * | 5/1996 | Fuisz ......................... 424/426 |
| 5,540,917 A | * | 7/1996 | Isler et al. ............... 424/78.01 |
| 5,576,306 A | * | 11/1996 | Dressman et al. ............ 514/57 |
| 5,643,874 A | | 7/1997 | Bremer et al. |
| 5,691,369 A | * | 11/1997 | Pelosi, Jr. et al. .......... 514/392 |
| 5,789,393 A | | 8/1998 | Dressman et al. ............ 514/57 |
| 6,030,953 A | | 2/2000 | Bailly et al. ................. 514/25 |
| 6,120,803 A | * | 9/2000 | Wong et al. ................. 424/473 |
| 6,126,969 A | * | 10/2000 | Shah et al. ................. 424/468 |
| 6,319,520 B1 | * | 11/2001 | Wuthrich et al. ........... 424/482 |
| 6,350,469 B1 | | 2/2002 | Daggy et al. ............... 424/464 |
| 6,358,522 B1 | | 3/2002 | Hug et al. ................... 424/441 |
| 6,372,253 B1 | | 4/2002 | Daggy et al. ............... 424/465 |
| 2002/0086052 A1 | | 7/2002 | Daggy et al. ............... 424/465 |

FOREIGN PATENT DOCUMENTS

| | | | |
|---|---|---|---|
| WO | WO 00/09122 | 2/2000 | ......... A61K/31/365 |
| WO | WO 00/09123 | 2/2000 | ......... A61K/31/365 |

* cited by examiner

*Primary Examiner*—Thurman K. Page
*Assistant Examiner*—S. Tran
(74) *Attorney, Agent, or Firm*—Theodore R. Furman, Jr.; Charles M. Kinzig; Stephen Venetianer

(57) ABSTRACT

The present invention relates to a novel pharmaceutical composition and process for preparing swallowable rapidly disintegrating methylcellulose and lipstatin derivatives together in combination with a suitable diluent and excipients.

24 Claims, No Drawings

LIPSTATIN DERIVATIVE-SOLUBLE FIBER TABLETS

This application is the §371 national stage entry of PCT/US99/20744, filed Sep. 8, 1999, which claims the benefit of priority from provisional application U.S. Ser. No. 60/099,399, filed Sep. 8, 1998.

FIELD OF THE INVENTION

The present invention relates to a preparation containing lipase inhibitors and soluble fibers compressed into a rapidly disintegrating tablet which meets USP disintegration standards.

BACKGROUND OF THE INVENTION

Orlistat, tetrahydrolipostatin, is a hypolipaemic lipstatin derivative, presently under development by Roche under the tradename Xenical®. Orlistat is a potent and selective inhibitor of pancreatic lipase. It also creates a fat phase in the intestine and removes endogenous cholesterol from bile in the intestine (Scrip, 1993, 1850, 12 & 1996, 2135, 22; Ann Rep, Roche, 1993). The lipase inhibitors act within the GI tract to inhibit the enzymes which hydrolyze dietary fat to glycerol and fatty acids. This hydrolysis is the required first step for fat digestion, and enables the absorption of lipids and fats, and their subsequent utilization for energy metabolism. Inhibition of fat digestion by lipase inhibitors such as orlistat, prevents fat absorption and hence, the availability of calories from ingested lipid.

Orlistat prevents the absorption of about one third of the fat contained in food (Ann Rep, Roche, 1995). The drug has undergone numerous placebo-controlled clinical studies, involving over 5000 obese patients. Orlistat resulted in significant weight loss and had no major adverse side-effects. During the first year of a two year study, 3-times as many patients on orlistat (with a moderately reduced calorie diet) lost 10% or more body weight as compared to patients treated with placebo and diet alone. Most patients who continued into the 2nd year of the study kept the lost weight off (Scrip, 1996, 2188, 17; Press release, Roche, May 1997). The drug is also being studied in patients with Type II diabetes (Ann Rep, Roche, 1992). The first year results of a 2 year study have shown that 228 patients receiving orlistat 3× daily as well as following a mildly hypocaloric diet have lost 65% more weight than the placebo controlled group, with almost ⅓ having lost >10% of their bodyweight (Scrip, 1996, 2135, 22).

In diet-induced obese rats, orlistat at 27 mg/kg/day caused a marked loss of body weight (65 g) and a decrease in carcass fat (54 g), despite occurrence of mild hyperphagia (11%). Fat absorption decreased from 93–94% to 17–19%. Orlistat-treated rats showed decreases in liver (13%) and retroperitoneal (RP) pad weight and an increase in small (27%) and large (38%) intestine weight (Fed Proc. 1987, 46, 1537).

The class of lipstatin inhibitors, which includes orlistat, inhibit enzymatic cleavage of fat within the intestinal lumen and largely prevents fat absorption from the intestine. Lipstatin inhibitors may be added at 0.1–100 mg ranges as a dietary additive to feedstuffs (esp. for dogs or cats) to prevent or treat adiposity and to optimize the weight of the animal. Use of these inhibitors with water insoluble fiber may further reduce fat resorption and is the subject of U.S. Pat. No. 5,540,917. Dose of orlistat plus water insoluble fiber reduces absorption of fat from the feedstuff by 1–100 (esp. 40–70)%. U.S. Pat. No. 5,540,917 does however, require large amounts of crude fiber to fat as the desired fiber content is 2–3× the fat content intake.

The lipase inhibitors act peripherally to inhibit fat digestion, and lack CNS side-effects. Their major side-effect is the potential to cause steatorrhea, anal oil leakage and incontinence, flatulence, and GI distress.

There exists in the art, the need to develop a product which would allow human patients—to sustain a treatment regiment of the lipostatin derivatives, but reduce the potential side effects, such as anal leakage, or at least minimize them. A combination a product which would reduce these side effects would also provide for an easily administered product, which is convenient to take and transport.

SUMMARY OF THE INVENTION

The present invention relates to a readily dispersible, rapidly disintegrating tablet which meets United States Pharmacopoeia standards and includes a lipstatin inhibitor, and a water soluble, non-fermentable cellulose derivative, preferably methylcellulose. The lipase inhibitors are preferably selected from among lipstatin derivatives, such as the compound tetrahydrolipostatin (orlistat). These two components are compressed into a tablet which further contain suitable diluents, in preferred w/w ratios. Preferred diluents for use with methylcellulose are edible calcium salts, such as dicalcium phosphate, dihydrate.

DETAILED DESCRIPTION OF THE INVENTION

The need for a safe clinically effect anti-obesity compound appears to have been found in the lipase inhibitors, of which orlistat is one of several. The mode of action of the lipase inhibitors is by to block fat absorption by inhibiting gastric and pancreatic lipase enzymes which break down fat molecules to smaller absorbable fatty acids and glycerol derivatives. When taken with a well-balanced, slightly hypocaloric diet, these inhibitors will inhibit absorption of approximately 30% of ingested fat.

The weight loss obtained with clinically effective doses of orlistat are approximately the same as those obtained with CNS-acting appetite suppressant drugs, such as fenfluramine, dexfenfluramine and sibutramine (5–10% of bodyweight in 1 year). While these drugs have potential CNS, and other, toxicities these are not an issue with the lipase inhibitors as they are not absorbed from the gastrointestinal tract. However, these inhibitors do have their own side-effect issues which are gastrointestinal tract in nature. These effects can range from mild diarrhea to faecal incontinence, as well as nausea, vomiting, flatulence, abdominal pain, liquid stools, and oily stools.

While patients may find some of these side effects tolerable, others, particularly faecal incontinence and steatorrhea, are not.

The present invention, therefore provides for a swallowable solid dosage form of a combination product which contains a bulking soluble fiber, preferably methylcellulose, which is convenient to take and transport, is preferably sugar free, and a lipstatin derivative, preferably orlistat. This tablet will be easily administered to the consumer who will not need to carry and ingest a powder diluted with water along with the orlistat tablet, but preferably will have the combined tablet in one dosage form. This becomes an ideal formulation to assist in patient compliance, and to help control the undesired side effects of the lipstatin inhibitors.

Therefore, one aspect of the present invention is a pharmaceutical composition comprising:

(a) at least one water soluble, non-fermentable cellulose derivative;
(b) at least one lipase inhibitor in an amount effective for treating adiposity; and
(c) at least one excipient which is selected from an edible calcium salt; or mixtures thereof.

The lipase inhibitor is selected from: (i) a lipstatin in pure form; (ii) a biomass comprising a lipase inhibitor, the biomass being obtained by a process of fermenting a fermentation broth comprising a microorganism which produces the lipase inhibitor and separating the biomass from the fermented broth; or (iii) tetrahydrolipstatin.

Suitable lipase inhibitors, such as lipstatin and analogues thereof, tetrahydrolipstatin and N-formyl-L-leucine (S)-1-[[(2S,3S)-3-ethyl-4-oxo-2-oxetanyl]methyl]octadecylester may be used in this invention, and are described in EP 129 748, EP 185 359 and EP 444 482 respectively. Additional lipase inhibitors are esterastin and its derivatives found in U.S. Pat. Nos. 4,189,438 and 4,202,824 and biomasss or fermentation cakes obtained in the fermentative production of lipase inhibitors, such as lipstatin or esterastin are described in EP 129 748 and U.S. Pat. No. 4,189,438 whose disclosures are incorporated herein by reference in their entirety.

In an alternative embodiment of the present invention, another aspect of the present invention is a pharmaceutical composition comprising:
(a) at least one water soluble, non-fermentable cellulose derivative;
(b) at least one lipase inhibitor in an amount effective for treating adiposity; and
(c) at least one swellable diluent or filler, such as but not limited to various grades of microcrystalline cellulose, such as Avicel PH101, Avicel PH 102 & Avicel PH 200; corn starch; or Starch 1500.

Preferably the diluent in this formulation is microcrystalline cellulose. A preferred size of microcrystalline cellulose is from about 50 to 180 micron, more preferably about 50. Avicel PH 101 has a mean particle size of about 50; Avicel PH 102 has a mean particle size of about 100; and Avicel PH 200 has a mean particle size of about 190 microns. Preferably the preferred microcrystalline cellulose is Avicel PH 101.

It is noted that the ratio of methylcellulose to the swellable diluent will depend upon the diluent chosen, and is within the skill of the art to determine with preciseness the necessary ratios.

Suitable ratios for particular diluents are described below, however, to provide greater assistance (in % w/w) ratios:

For Methylcellulose: microcrystalline cellulose, from about 2:1 to about 14:1.
Preferably, for Avicel PH 101 from about 2.2–13.5:1; for Avicel PH 102 from about 2.4–8.3:1; and for Avicel PH 200 from about 2.4–4:1.
For Methylcellulose:Corn starch from about 7.5 to about 15, preferably from about 13.5:1; and
For Methylcellulose:Starch 1500, from about 2.0 to about 5.0:1, preferably from about 2.4:1.

In addition to the above noted diluents or fillers, additional components include but are not limited to, a wetting agent, a (super)disintegrant, a binding agent, dye(s) or colouring agents, and lubricants, are preferably used to prepare a tablet that is wetted readily, and is rapidly disintegrated in 0.1N hydrochloric acid and water, the USP test standard test for methylcellulose.

Preferred additional agents for these swellable diluent pharmaceutical composition are similar to those discussed below for the compositions containing the edible calcium salts.

Another aspect of the present invention is the method for dual treatment of adiposity and the faecal incontinence and steatorrhea associated therewith using a compressed tablet formulation of
(a) at least one water soluble, non-fermentable cellulose derivative;
(b) at least one lipase inhibitor in an amount effective for treating adiposity; and
(c) at least one excipient which is selected from an edible calcium salt; or mixtures thereof.

Another aspect of the present invention is the method for dual treatment of adiposity and the faecal incontinence and steatorrhea associated therewith using a compressed tablet formulation of
(a) at least one water soluble, non-fermentable cellulose derivative;
(b) at least one lipase inhibitor in an amount effective for treating adiposity; and
(c) at least one swellable diluent or filler, such as but not limited to various grades of microcrystalline cellulose, such as Avicel PH101, Avicel PH 102 & Avicel PH200; corn starch; or Starch 1500.

The dosage of orlistat in either the edible salt or swellable diluent formulation is recommended to be about 120 to 125 mg three times daily, which dosage can conveniently be formulated in a 250 to 500 mg methylcellulose tablet as described herein. However, it is recognized that in some individuals a higher dosage might be necessary, such as 50 to 250 mg three times daily, preferably 100–200 mg, more preferably 110–150 mg.

To accommodate this dosage range with the non-fermentable cellulose a tablet containing about 40 to 70, preferably about 50 to 60 mg of orlistat with about 450–500 mg methylcellulose. This would hopefully provide translate to a total daily dose of orlistat of 150 to 750 mg/day, preferably 300–600 mg/day, and more preferably about a dose of 330 to 450 mg/day range on mg/Kg basis (assuming a 75 Kg person) is 4.4 mg/kg-day to 6 mg/Kg-day, under the most optimal conditions.

A preferred non-fermentable cellulose for use herein is methylcellulose having a viscosity of >1000 centipoise. Lower molecular weight (mw) methylcellulose is less desirable for use in a rapidly disintegrating tablet formulation.

By using the testing methods for methylcellulose under standard conditions, such as those found in the USP XXII, p. 894, Apparent Viscosity method for Methylcellulose, or as discussed in Handbook of Pharmaceutical Excipients, APhA, a preferred methylcellulose for use herein should have a viscosity of >1000 centipoises (cps), preferably >2000 centipoises, more preferably >3000 centipoises, and most preferably >4000 centipoise. Higher molecular weight methylcellulose than those described is also desirable, however, the commercially availability of this grade of methylcellulose being the limiting feature. At present the upper limit commercially available is about 6000 cps, which is encompassed within the scope of this invention. One presently available methylcellulose product for use herein is Methocel A4M, made by Dow Chemical Company, Midland, Mich. as Dow Methocel A4M, having a viscosity of about 3000 to about 5,600 cps, which is within 75 to 140% of the desired target viscosity herein.

The edible calcium salts suitable for use herein include but are not limited to, dibasic calcium phosphate dihydrate, calcium phosphate anhydrous, and tribasic calcium phosphate; or mixtures thereof. A preferred edible calcium salt is the dibasic calcium phosphate dihydrate salt, which salt also provides good compressibility.

The edible calcium salt formulation may contain additional diluents or fillers which are preferably swellable agents (such as used alone in the alternative formulation), and may include, but are not limited to, various grades of microcrystalline cellulose, such as Avicel PH101, Avicel PH102, & Avicel PH200; Corn starch, cornstarch derivatives, such as maltodextrin; or Starch 1500.

In either formulation, if microcrystalline cellulose is added, it is preferably from about 50 to 180 microns in size, more preferably about 50. Avicel PH 101 has a mean particle size of about 50; Avicel PH 102 has a mean particle size of about 100; and Avicel PH 200 has a mean particle size of about 190 microns. Preferably the preferred microcrystalline cellulose is Avicel PH 101.

It is noted that the ratio of methylcellulose to edible calcium salt, and additional diluents will depend upon the diluent chosen, and is within the skill of the art to determine with preciseness the necessary ratios.

In formulating the compressed tablet suitable ratios for particular diluents are described below (in % w/w) ratios:

Suitable ratios for particular diluents however, are described below:

For Methylcellulose:Dibasic calcium phosphate, dihydrate, from about 2 to about 4:1, preferably from about 2.6–3.1:1;
For Methylcellulose:Calcium phosphate, anhydrous from about 2 to about 4:1, preferably from about 3.1:1;
Methylcellulose:Tribasic calcium phosphate, WG® from about 2 to about 4:1, preferably from about 3.1:1.

It is recognized that with the edible calcium salt, the formulation must also have an ingredient which keeps the granules together, i.e. a binding agent. A preferred binding agent is PVP, or the alternative agents noted below.

In addition to the above noted edible calcium salt(s), optional diluents or fillers, and binding agent(s), the formulation may also include additional components such as, but are not limited to, a wetting agent, (super)disintegrant(s), a second binding agent(s), dye(s) or colouring agents, and lubricants, which are preferably used to prepare a tablet that is wetted readily, and is rapidly disintegrated in 0.1N hydrochloric acid and water, the USP test standard test for methylcellulose.

A preferred wetting agent is sodium lauryl sulfate.
A preferred lubricant is magnesium stearate.
A preferred binding agent is polyvinylpyrrolidone, or PVP, such as Povidone 29K/32. Preferably, the PVP is present in an amount of about 4 to about 6.5% w/w.
A preferred disintegrating agent is sodium starch glycolate, such as Explotab®. Preferably, the sodium starch glycolate is present in an amount of about 3 to about 8% w/w.

As various excipients and diluents will be formulated together, and used in combination herein, suggested % w/w ratios for various formulations are presented below. These ratios are merely illustrative of the present invention and the skilled artisan will readily recognize how to formulate the product of this invention with the addition of edible calcium or the swellable diluent (where desired).

Sodium lauryl sulfate:Explotab:Dibasic calcium phosphate, dihydrate:Povidone 29K/32:Magnesium stearate include: 0.38–0.40:3.5–7.9:20.6–24.8:4.0–6.5:0.5–1.0

Sodium lauryl sulfate:Explotab:Tribasic calcium phosphate WG®: Povidone 29K/32:Magnesium stearate include: 0.40:3.5:21.6:6.4:1.0
Sodium lauryl sulfate:Explotab:Calcium phosphate, anhydrous: Povidone 29K/32:Magnesium stearate include: 0.40:3.5:21.6:6.4:1.0
Methylcellulose:sodium lauryl sulfate (SLS), from about 60 to about 170:1. preferably from about 155:1–170:1;
Methylcellulose:Povidone, preferably PVP 29K/32, from about 8 to about 22:1, preferably from about 10.4:1–16.7:1;
Methylcellulose:Magnesium stearate from about 50 to about 150; 1, preferably from about 58–132:1:
Sodium lauryl sulfate:Explotab:Avicel PH 101®: Povidone 29K/32:Magnesium stearate include: 0.35–0.46:3.05–6.17:4.38–27.13:4.38–6.66:0.76–1.14
Sodium lauryl sulfate:Explotab:Avicel PH 102®: Povidone 29K/32:Magnesium stearate include: 0.35–0.46:4.9–6.17:9.21–25.53:4.38–6.66:0.76–1.14
Sodium lauryl sulfate:Avicel PH 200®: Povidone 29K/32:Magnesium stearate include: 0.38–0.42:19.27–25.53:5.99–6.66:0.94–1.04
Sodium lauryl sulfate:Explotab:Corn starch: Povidone 29K/32:Magnesium stearate include: 0.36–0.38:3.66–7.07:4.35–4.68:4.35–4.68:0.88–0.95
Sodium lauryl sulfate:Explotab:Starch 1500®: Povidone 29K/32:Magnesium stearate include: 0.36–0.38:3.66–7.07:24.05–25.89:4.354.68:0.88–0.95

Another advantageous property of the present invention is that some of these formulations contain calcium, such as dibasic calcium phosphate dihydrate. These formulations, for instance, will contain approximately an 80 mg/dose, anticipating formulating a 0.5 gm/tablet×2 tablets/dose of methylcellulose. If desired the amount of calcium can be increased in these tablets to provide increased therapeutic value to the consumer.

As will readily be seen by the working examples, there are various combinations of intra and extragranular mixing which are possible using the ingredients herein. All are encompassed within the scope of this invention. Generally, the high viscosity methylcellulose, such as Methocel A4M, will first be granulated with a binder, such as povidone, a wetting agent, such as sodium lauryl sulfate, and a suitable colouring agent to form the intragranular mixture which is then granulated. These granular components are then admixed with additional wetting agents, and disintegrating agents and finally blended with lubricant. This final granular mixture is then blended and compressed into the tablets of the present invention.

Historically, cellulose ethers, such as methylcellulose and carboxymethylcellulose have been taught as being effective bulk laxative agents. Their mechanism of action involves increasing both the water content of, and the bulk content of the stool, as well as lubricating the stool; thereby relieving constipation.

Cellulose ethers have been administered as bulk laxatives in dosage forms comprising of tablets, suspensions, and bulk powders; the latter as sugar-free or in compositions containing high amounts of sugar.

Other bulking may also be used in combination with this invention for use in reducing loose stools and diarrhea. The same property, binding water and fluid into a gel matrix, which provides stool softening in constipation, will also work to reduce stool liquidity in diarrhea.

Cellulose ethers administered as suspensions in water may contain high concentrations of sucrose or other sugars and flavors. In such formulations, the sugar competes with the cellulose ether for available water, thereby preventing the cellulose ether from hydrating sufficiently to form a gel. Furthermore, the added calories from the high level of sugars would be disfavored for use in a weight control therapy. Finally these suspensions are viscous, semi-gelatinous, visually unappealing to patients, and have poor palatability. Similarly, bulk powders of cellulose ethers often exhibit clumping of individual particles, which thus remain undissolved as they pass through the digestive tract. This could reduce bioavailability of the added lipstatin inhibitor.

There is a common belief that tableted cellulose ethers do not readily dissolve in the digestive tract because these cellulose ethers are highly hygroscopic. The outer portion of the tablet is said to form a gel-like hydrate that prevents the tablet from breaking up and greatly retards the hydration of the inner portion of the tablet.

These semi-synthetic fibers, i.e. water soluble, non-fermentable cellulose derivatives (e.g., methylcellulose, ethylcellulose, carboxymethylcellulose, hydroxypropyl-methylcellulose) have been in the food supply for decades, and are considered safe, but the beneficial clinical effects of these fibers has not been considered in the area of laxation as a compressed tablet, due to their failure to disintegrate.

The present invention overcomes this art recognized problem and involves preparation of a novel composition for the water soluble, non-fermentable fiber, in combination with a lipase inhibitor, and process of making such.

The tablets of this invention are prepared by a novel process involving a high-shear wet granulation method, followed by fluidized bed drying, milling, mixing with the other ingredients, and compression. As noted above, preferably, all excipients employed to prepare the tablets of this invention are sugar-free.

This invention therefore, provides for a novel dosage form of the above noted semi-synthetic fibers, preferably methylcellulose, with a suitable lipstatin derivative, preferably orlistat, for convenience of administration and for its ability to have rapid disintegration.

These tablets, in contrast to other tablets of methylcellulose, which have been previously formulated as 100% w/w methylcellulose in a 0.5 gm caplet have been found not to disintegrate in 0.1N HCL solution, using a conventional dissolution apparatus even after two hours. Target tablet hardness desired is between 10 and 25, preferably 8–12 SCU; a preferred target weight of each tablet of less than 750 mg; an estimated friability of less than 2.0%, more preferably less than 1.0%, and target disintegration times below 30 minutes in water and acid (shorter disintegration times, less than 10 minutes, more preferably less than 8 minutes, in 0.1N HCl and less than 15 minutes in water, more preferably about 8 minutes, are preferred).

As will readily be seen by the working examples, there are various combinations of intra and extragranular mixing which are possible using the ingredients herein. All are encompassed within the scope of this invention. Generally, the high viscosity methylcellulose, such as Methocel A4M, will first be granulated with the lipstatin derivative; a suitable diluent, such as microcrystalline cellulose; a binding agent, such as povidone; a wetting agent, such as sodium lauryl sulfate; and optionally a suitable colouring agent to form the intragranular mixture which is granulated. These granular components are then admixed with the lubricants, additional wetting agents, disintegrating agents, and any additional agents so desired. This final granular mixture is then compressed into the tablets of the present invention.

Therefore, one aspect of this invention is a process for the manufacture of a pharmaceutical tablet, which process comprises mixing a) granulates comprising high viscosity methylcellulose of >3000 cps; a diluent selected a diluent selected from microcrystalline cellulose, corn starch, or Starch 1500, or a mixture thereof; a lipase inhibitor, and optionally together with an intra-granular disintegrant, and/or wetting agent, and/or colouring agent; with b) an extra-granular disintegrant, and wetting agent, and optionally an extra-granular lubricant and excipient(s); and c) compressing into a tablet.

More preferablly, is the preparation of a tablet formulation which process comprises:

a) blending together to form an intragranular mixture high viscosity methylcellulose of >3000 cps; a diluent selected from microcrystalline cellulose, corn starch, or Starch 1500, or a mixture thereof; a lipase inhibitor; a lubricating agent; and optionally a disintegrant; and b) adding to the mixture of step (a), a PVP aqueous solution, or alternatively spraying the mixture of step (a) with a PVP aqueous solution; and preparing granulates; and c) blending together an extragranular mixture of a wetting agent; a lubricating agent; a diluent; and a disintegrant, or a mixture thereof; and d) compacting the granulates of step (b) with the extra-granular mixture of step (c).

Yet an alternative embodiment of this invention is the admixture of the lipase inhibitor in at step c) rather than step a).

Preferably, in this process the extragranular components includes microcrystalline cellulose, sodium lauryl sulfate, sodium starch glycolate, and magnesium stearate. Alternatively, the extragranular components are starch, sodium lauryl sulfate, sodium starch glycolate, and magnesium stearate. A prefered range of sodium starch glycolate is from about 3 to about 8% w/w.

Another aspect of this invention is a process for the manufacture of a pharmaceutical tablet, which process comprises mixing a) granulates comprising high viscosity methylcellulose of >3000 cps; at least one edible calcium salt. or mixtures thereof; a lipase inhibitor, and optionally together with an intra-granular disintegrant, and/or wetting agent, and/or colouring agent; with b) an extra-granular disintegrant, and wetting agent, and optionally an extra-granular lubricant and excipient(s); and c) compressing into a tablet.

An alternative embodiment of this invention is the admixture of the lipase inhibitor in step b) rather than step a), and similarly to the preferred process below.

More specifically, the process may include, preparation of a tablet formulation which process comprises:

a) blending together to form an intragranular mixture high viscosity methylcellulose of >3000 cps; at least one edible calcium salt, or mixtures thereof; a lipase inhibitor; a lubricating agent; and optionally a disintegrant; and b) adding to the mixture of step (a), a PVP aqueous solution, or alternatively spraying the mixture of step (a) with a PVP aqueous solution; and preparing granulates; and c) blending together an extragranular mixture of a wetting agent; a lubricating agent; a diluent; and a disintegrant, or a mixture thereof; and d) compacting the granulates of step (b) with the extragranular mixture of step (c).

Therefore, another aspect of the present invention is the granulates of the lipstatin derivative, the water soluble, non-fermentable cellulose derivative and suitable diluents and excipients as described herein.

Therefore, another aspect of the present invention is the granulates of the lipstatin derivative, the water soluble, non-fermentable cellulose derivative and suitable diluents and excipients as described herein.

Yet another aspect of the present invention is the method of relieving faceal incontinence or anal leakage in a mammal in need thereof, which method comprises administering to said mammal, an effective amount of a water soluble, non-fermentable cellulose derivative, preferably a high viscosity methylcellulose, compressed into a tablet with a suitable diluent as is described above. This composition optionally includes an effective amount of a lipstatin derivative, such as orlistat.

METHODS OF PREPARATION

The following examples illustrates the invention but is not intended to limit the scope thereof. All parts and percentages are by weight unless otherwise indicated. The disintegration time of the formulations described in the Tables below were obtained by using a conventional disintegration apparatus.

EXAMPLE 1

TABLE I

Swallowable Methylcellulose Tablets

| Formula Ingredient | g/tablet | (% w/w) |
|---|---|---|
| Phase A | | |
| Methocel A4M | 0.5000 | 62.64 |
| Dibasic Calcium phosphate, dihydrate | 0.0370 | 4.61 |
| Sodium lauryl sulfate | 0.0015 | 0.19 |
| Dye/Colouring agent | 0.0010 | 0.12 |
| Povidone 29K/32 | 0.0480 | 5.98 |
| Tetrahydrolipstatin | 0.060 | 7.47 |
| DI water | q.s. | q.s. |
| Phase B | | |
| Phase A | 0.5875 | 73.14 |
| Sodium lauryl sulfate | 0.0015 | 0.19 |
| Sodium starch glycolate | 0.0260 | 3.24 |
| Dibasic Calcium phosphate, dihydrate | 0.1245 | 15.50 |
| Magnesium stearate | 0.0038 | 0.47 |
| TOTAL | 0.8033 | 100.00 |

The process of preparing the rapidly disintegrating tablet of methylcellulose is carried out using specified quantities of ingredients, such as those mentioned in TABLE I above, using the following steps:

1. Preparation of Povidone K29/32 (PVP) Solution

The specified amount of PVP is weighed and added to the weighed quantity of water and stirred till all the PVP was dissolved completely.

2. Preparation of Phase A

Accurately weighed amounts of Methocel A4M, calcium phosphate, dibasic dihydrate, sodium lauryl sulfate, lipase inhibitor, and colouring agent, such as any suitable FD&C Aluminum lake, are transferred to a Key Hi-shear granulator and mixed for about 10 minutes with impellor speed at 135 rpm and chopper speed at 10%. The PVP solution is sprayed onto the mixture in the granulator at a rate of approx. >200 mL/min. Once addition of PVP solution is complete, the chopper is stopped. The mixing is continued in the granulator till resistance reads about 130–135 watts and the time noted to reach that wattage. A sample is withdrawn from the wet granulation to record loss on drying (% LOD). The moist granules are dried in the Aeromatic Fluid bed dryer in portions till the % LOD reading approximated 1.0–3.0%. The temperature of the air in the fluid bed dryer is maintained at approx. 90–95° C. and the sample is found to be dry at an outlet air temperature of approx. 32–52° C. The dried granules are milled through a 12# screen in the Fitz Mill at a high speed. The granules are weighed and percent yield calculated. The moisture content is measured for the dry granules. A sample from the granules is withdrawn and analyzed for particle size distribution, bulk and tap density, flow index, and moisture studies. The granules are weighed and ingredients of Phase B are calculated based on the weight of remaining granules.

3. Preparation of the Final Blend

To the weighed milled granules produced in Phase A above, specified amounts of sodium lauryl sulfate, sodium starch glycolate (Explotab®), and dibasic calcium phosphate, dihydrate are added into the V-blender and mixed for about 10 minutes. Magnesium stearate is then added to the blend and mixed for an additional 3 minutes or so. Samples from different sections of the V-blender are drawn and submitted to for analyzing blend uniformity. A sample from the final blend is analyzed for particle size distribution, bulk and tap density, flow index, and moisture studies. The granules are then weighed.

4. Compression of Methylcellulose Tablets

The final blend is charged into the hopper of a Stokes single punch 'F' tablet press and compressed into caplets with a suitable tooling. The desired target hardness is 18–21 SCU, estimated friability desired is less than 1.0% and target disintegration time below 30 minutes (shorter disintegration times. around 3 to 8 minutes in 0.1N HCl and 8–15 minutes in water is preferred). The tablets are packaged in Ziplock bags. The tablets are tested for weight variation, hardness, disintegration in acid and water, friability, moisture (% LOD), thickness, viscosity, and content uniformity.

The disintegration time for the formulation of Table 1, Example 1, without orlistat, was less than 5 minutes in 0.1N HCl, and less than 9 minutes in water.

EXAMPLE 2

The above formulation, Example 1, demonstrates how to prepare a suitable methycellulose rapidly disintegrating tablet which includes a lipase inhibitor. As this active agent will remain constant throughout these examples, Examples 2 through 23 describe suitable rapidly disintegrating tablet formulations to which an effective amount of a lipase inhibitor, preferably orlistat may be added in an analogous manner to that shown above for Example 1.

In Example 2, a formulation containing both Avicel PH 101® and Explotab®, intra and extragranularly is shown in TABLE II below.

The lipase inhibitor is shown as being added to the Phase A. It is, however, recognized that a skilled artisan may alternatively formulate the lipase inhibitor in Phase B using similar ingredients, ratios and amounts to those examples described herein.

TABLE II

Swallowable Methylcellulose Tablets

| Formula Ingredient | g/tablet | (% w/w) |
|---|---|---|
| Phase A | | |
| Methocel A4M | 0.5000 | 60.31 |
| Avicel PH 101 ® | 0.0370 | 4.46 |
| Sodium lauryl sulfate | 0.0015 | 0.18 |
| Povidone 29K/32 | 0.0370 | 4.46 |
| Explotab ® | 0.0300 | 3.62 |
| DI water | q.s. | q.s. |
| Phase B | | |
| Phase A | 0.6055 | 73.03 |
| Sodium lauryl sulfate | 0.0017 | 0.21 |
| Sodium starch glycolate | 0.0253 | 3.05 |
| Avicel PH 101 ® | 0.1880 | 22.67 |
| Magnesium stearate | 0.0086 | 1.04 |
| TOTAL | 0.8291 | 100.00 |

EXAMPLE 3

A formulation containing Avicel PH 101® intragranularly, extragranular Avicel PH 102® and Explotab®, intra and extragranularly, is shown below.

TABLE III

Swallowable Methylcellulose Tablets

| Formula Ingredient | g/tablet | (% w/w) |
|---|---|---|
| Phase A | | |
| Methocel A4M | 0.5000 | 59.24 |
| Avicel PH 101 ® | 0.0370 | 4.38 |
| Sodium lauryl sulfate | 0.0015 | 0.18 |
| Povidone 29K/32 | 0.0370 | 4.38 |
| Explotab ® | 0.0300 | 3.56 |
| Dye/colouring agent | 0.0040 | 0.47 |
| DI water | q.s. | q.s. |
| Phase B | | |
| Phase A | 0.6095 | 72.21 |
| Sodium lauryl sulfate | 0.0015 | 0.18 |
| Sodium starch glycolate | 0.0220 | 2.61 |
| Avicel PH 102 ® | 0.2035 | 24.11 |
| Magnesium stearate | 0.0075 | 0.89 |
| TOTAL | 0.8440 | 100.00 |

EXAMPLE 4

A formulation containing Avicel PH101® intragranularly, extragranular Avicel PH 102® and Explotab® intra and extragranularly is shown in TABLE IV below.

TABLE IV

Swallowable Methylcellulose Tablets

| Formula Ingredient | g/tablet | (% w/w) |
|---|---|---|
| Phase A | | |
| Methocel A4M | 0.5000 | 59.52 |
| Avicel PH 101 ® | 0.0370 | 4.41 |
| Sodium lauryl sulfate | 0.0015 | 0.18 |
| Povidone 29K/32 | 0.0370 | 4.41 |
| Explotab ® | 0.0300 | 3.57 |
| DI water | q.s. | q.s. |
| Phase B | | |
| Phase A | 0.6055 | 72.08 |
| Sodium lauryl sulfate | 0.0015 | 0.18 |
| Sodium starch glycolate | 0.0220 | 2.62 |
| Avicel PH 102 ® | 0.2035 | 24.23 |
| Magnesium stearate | 0.0075 | 0.89 |
| TOTAL | 0.8400 | 100.00 |

EXAMPLE 5

A formulation containing Avicel PH101® intragranularly, extragranular Avicel PH 102® and Explotab® intra and extragranularly is shown below in TABLE V.

TABLE V

Swallowable Methylcellulose Tablets

| Formula Ingredient | g/tablet | (% w/w) |
|---|---|---|
| Phase A | | |
| Methocel A4M | 0.5000 | 60.24 |
| Avicel PH 101 ® | 0.0370 | 4.46 |
| Sodium lauryl sulfate | 0.0015 | 0.18 |
| Povidone 29K/32 | 0.0370 | 4.46 |
| Explotab ® | 0.0300 | 3.62 |
| DI water | q.s. | q.s. |
| Phase B | | |
| Phase A | 0.6055 | 72.95 |
| Sodium lauryl sulfate | 0.0015 | 0.18 |
| Sodium starch glycolate | 0.0110 | 1.33 |
| Avicel PH 102 ® | 0.2045 | 24.64 |
| Magnesium stearate | 0.0075 | 0.90 |
| TOTAL | 0.8300 | 100.00 |

EXAMPLE 6

A formulation containing Avicel PH101® intragranularly, extragranular Avicel PH102® and no Explotab® is shown in TABLE VI below.

TABLE VI

Swallowable Methylcellulose Tablets

| Formula Ingredient | g/tablet | (% w/w) |
|---|---|---|
| Phase A | | |
| Methocel A4M | 0.5000 | 67.94 |
| Avicel PH 101 ® | 0.0370 | 5.03 |
| Sodium lauryl sulfate | 0.0015 | 0.20 |
| Povidone 29K/32 | 0.0370 | 5.03 |
| Dye/Colouring Agent | 0.0010 | 0.14 |
| DI water | q.s. | q.s. |
| Phase B | | |
| Phase A | 0.5765 | 78.34 |
| Sodium lauryl sulfate | 0.0011 | 0.15 |

TABLE VI-continued

Swallowable Methylcellulose Tablets

| Formula Ingredient | g/tablet | (% w/w) |
|---|---|---|
| Avicel PH 102 ® | 0.1527 | 20.75 |
| Magnesium stearate | 0.0056 | 0.76 |
| TOTAL | 0.7359 | 100.00 |

EXAMPLE 7

A formulation containing corn starch intragranularly, extragranular Starch 1500 and no Explotab® is shown below in TABLE VII.

TABLE VII

Swallowable Methylcellulose Tablets

| Formula Ingredient | g/tablet | (% w/w) |
|---|---|---|
| Phase A | | |
| Methocel A4M | 0.5000 | 63.29 |
| Corn starch | 0.0370 | 4.68 |
| Sodium lauryl sulfate | 0.0015 | 0.19 |
| Povidone 29K/32 | 0.0370 | 4.68 |
| Dye/Colouring Agent | 0.0010 | 0.13 |
| DI water | q.s. | q.s. |
| Phase B | | |
| Phase A | 0.5765 | 72.97 |
| Sodium lauryl sulfate | 0.0015 | 0.19 |
| Starch 1500 ® | 0.2045 | 25.89 |
| Magnesium stearate | 0.0075 | 0.95 |
| TOTAL | 0.7900 | 100.00 |

EXAMPLE 8

A formulation containing corn starch intragranularly, extragranular Starch 1500 and intragranular Explotab® as shown below in TABLE VIII.

TABLE VIII

Swallowable Methylcellulose Tablets

| Formula Ingredient | g/tablet | (% w/w) |
|---|---|---|
| Phase A | | |
| Methocel A4M | 0.5000 | 61.00 |
| Corn starch | 0.0370 | 4.51 |
| Sodium lauryl sulfate | 0.0015 | 0.18 |
| Povidone 29K/32 | 0.0370 | 4.51 |
| Explotab ® | 0.0300 | 3.66 |
| Dye/Colouring Agent | 0.0010 | 0.12 |
| DI water | q.s. | q.s. |
| Phase B | | |
| Phase A | 0.6065 | 73.98 |
| Sodium lauryl sulfate | 0.0015 | 0.18 |
| Starch 1500 ® | 0.2045 | 24.93 |
| Magnesium stearate | 0.0075 | 0.91 |
| TOTAL | 0.8200 | 100.00 |

EXAMPLE 9

A formulation containing corn starch intragranularly, extragranular Starch 1500 and intra as well as extragranular Explotab® is shown below in TABLE IX.

TABLE IX

Swallowable Methylcellulose Tablets

| Formula Ingredient | g/tablet | (% w/w) |
|---|---|---|
| Phase A | | |
| Methocel A4M | 0.5000 | 59.88 |
| Corn starch | 0.0370 | 4.43 |
| Sodium lauryl sulfate | 0.0015 | 0.18 |
| Povidone 29K/32 | 0.0370 | 4.43 |
| Explotab ® | 0.0300 | 3.59 |
| Dye/Colouring Agent | 0.0010 | 0.12 |
| DI water | q.s. | q.s. |
| Phase B | | |
| Phase A | 0.6065 | 72.63 |
| Sodium lauryl sulfate | 0.0015 | 0.18 |
| Starch 1500 ® | 0.2045 | 24.49 |
| Explotab ® | 0.0150 | 1.80 |
| Magnesium stearate | 0.0075 | 0.90 |
| TOTAL | 0.8350 | 100.00 |

EXAMPLE 10

A formulation containing corn starch intragranularly, extragranular Starch 1500 and intra as well as extragranular Explotab® (in higher amounts than shown above in Example 9, TABLE IX) is shown below in TABLE X.

TABLE X

Swallowable Methylcellulose Tablets

| Formula Ingredient | g/tablet | (% w/w) |
|---|---|---|
| Phase A | | |
| Methocel A4M | 0.5000 | 58.82 |
| Corn starch | 0.0370 | 4.35 |
| Sodium lauryl sulfate | 0.0015 | 0.18 |
| Povidone 29K/32 | 0.0370 | 4.35 |
| Explotab ® | 0.0300 | 3.53 |
| Dye/Colouring Agent | 0.0010 | 0.12 |
| DI water | q.s. | q.s. |
| Phase B | | |
| Phase A | 0.6065 | 71.35 |
| Sodium lauryl sulfate | 0.0015 | 0.18 |
| Starch 1500 ® | 0.2045 | 24.05 |
| Explotab ® | 0.0300 | 3.54 |
| Magnesium stearate | 0.0075 | 0.88 |
| TOTAL | 0.8500 | 100.00 |

EXAMPLE 11

Various formulation containing Avicel PH101® intragranularly and different levels of extragranular Avicel PH102® (as shown in Examples 6, 7, and 8 above) may be made.

TABLE XI

Swallowable Methylcellulose Tablets

| Formula Ingredient | g/tablet | (% w/w) |
|---|---|---|
| Phase A | | |
| Methocel A4M | 0.5000 | 62.42 |
| Avicel PH 101 ® | 0.0370 | 4.62 |
| Sodium lauryl sulfate | 0.0015 | 0.19 |
| Povidone 29K/32 | 0.0480 | 5.99 |
| Dye/Colouring Agent | 0.0010 | 0.12 |
| DI water | q.s. | q.s. |
| Phase B | | |
| Phase A | 0.5875 | 73.34 |
| Sodium lauryl sulfate | 0.0015 | 0.19 |
| Avicel PH 102 ® | 0.2045 | 25.53 |
| Magnesium stearate | 0.0075 | 0.94 |
| TOTAL | 0.8010 | 100.00 |

EXAMPLE 12

Various formulation containing Avicel PH101® intragranularly and different levels of extragranular Avicel PH102® may be made as shown below in Table XII.

TABLE XII

Swallowable Methylcellulose Tablets

| Formula Ingredient | g/tablet | (% w/w) |
|---|---|---|
| Phase A | | |
| Methocel A4M | 0.5000 | 69.35 |
| Avicel PH 101 ® | 0.0370 | 5.13 |
| Sodium lauryl sulfate | 0.0015 | 0.21 |
| Povidone 29K/32 | 0.0480 | 6.66 |
| Dye/Colouring Agent | 0.0010 | 0.14 |
| DI water | q.s. | q.s. |
| Phase B | | |
| Phase A | 0.5875 | 81.48 |
| Sodium lauryl sulfate | 0.0015 | 0.21 |
| Avicel PH 102 ® | 0.1245 | 17.27 |
| Magnesium stearate | 0.0075 | 1.04 |
| TOTAL | 0.7210 | 100.00 |

EXAMPLE 13

Various formulation containing Avicel PH101® intragranularly and different levels of extragranular Avicel PH102® may be made as shown below in Table XIII.

TABLE XIII

Swallowable Methylcellulose Tablets

| Formula Ingredient | g/tablet | (% w/w) |
|---|---|---|
| Phase A | | |
| Methocel A4M | 0.5000 | 76.10 |
| Avicel PH 101 ® | 0.0370 | 5.63 |
| Sodium lauryl sulfate | 0.0015 | 0.23 |
| Povidone 29K/32 | 0.0480 | 7.31 |
| Dye/coloring agent | 0.0010 | 0.15 |
| DI water | q.s. | q.s. |

TABLE XIII-continued

Swallowable Methylcellulose Tablets

| Formula Ingredient | g/tablet | (% w/w) |
|---|---|---|
| Phase B | | |
| Phase A | 0.5875 | 89.42 |
| Sodium lauryl sulfate | 0.0015 | 0.23 |
| Avicel PH 102 ® | 0.0605 | 9.21 |
| Magnesium stearate | 0.0075 | 1.14 |
| TOTAL | 0.6570 | 100.00 |

EXAMPLE 14

Two formulations containing Avicel PH101® intragranularly with different levels of extragranular Avicel PH200® (shown in TABLE XIV and XV below) may be made to observe the effect on disintegration time of tablets.

TABLE XIV

Swallowable Methylcellulose Tablets

| Formula Ingredient | g/tablet | (% w/w) |
|---|---|---|
| Phase A | | |
| Methocel A4M | 0.5000 | 62.42 |
| Avicel PH 101 ® | 0.0370 | 4.62 |
| Sodium lauryl sulfate | 0.0015 | 0.19 |
| Povidone 29K/32 | 0.0480 | 5.99 |
| Dye/Coloring Agent | 0.0010 | 0.12 |
| DI water | q.s. | q.s. |
| Phase B | | |
| Phase A | 0.5875 | 73.34 |
| Sodium lauryl sulfate | 0.0015 | 0.19 |
| Avicel PH 200 ® | 0.2045 | 25.53 |
| Magnesium stearate | 0.0075 | 0.94 |
| TOTAL | 0.8010 | 100.00 |

EXAMPLE 15

The second of the two formulations noted above containing Avicel PH101® intragranularly with different levels of extragranular Avicel PH 200® is shown below in TABLE XV.

TABLE XV

Swallowable Methylcellulose Tablets

| Formula Ingredient | g/tablet | (% w/w) |
|---|---|---|
| Phase A | | |
| Methocel A4M | 0.5000 | 69.35 |
| Avicel PH 101 ® | 0.0370 | 5.13 |
| Sodium lauryl sulfate | 0.0015 | 0.21 |
| Povidone 29K/32 | 0.0480 | 6.66 |
| Dye/Coloring Agent | 0.0010 | 0.14 |
| DI water | q.s. | q.s. |
| Phase B | | |
| Phase A | 0.5875 | 81.48 |
| Sodium lauryl sulfate | 0.0015 | 0.21 |

TABLE XV-continued

Swallowable Methylcellulose Tablets

| Formula Ingredient | g/tablet | (% w/w) |
|---|---|---|
| Avicel PH 200 ® | 0.1245 | 17.27 |
| Magnesium stearate | 0.0075 | 1.04 |
| TOTAL | 0.7210 | 100.00 |

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A pharmaceutical composition for an immediate release tablet comprising:
   (a) at least one water soluble, non-fermentable cellulose derivative which is methylcellulose having a viscosity of >1000 centipoise;
   (b) at least one lipase inhibitor in an amount effective for treating adiposity; and
   (c) at least one excipient which is an edible calcium salt which is dibasic calcium phosphate dihydrate, calcium phosphate anhydrous, or tribasic calcium phosphate; or mixtures thereof.

2. The composition according to claim 1 wherein the edible calcium salt is dibasic calcium phosphate dihydrate salt.

3. The composition according to claim 1 which further comprises a binding agent which is PVP, hydroxypropylcellulose, hydroxypropyl methylcellulose, acacia, gelatin, tragacanth, pregelatinized starch, or starch.

4. The composition according to claim 1 which further comprises a disintegrating agent which is sodium starch glycolate, sodium carboxymethylcellulose, internally crosslinked sodium carboxymethylcellulose, carboxymethylcellulose, veegum, alginates, agar, guar, tragacanth, locust bean, karaya, pectin, or crospovidone.

5. The composition according to claim 1 which further comprises a wetting agent, and/or a lubricating agent.

6. The composition according to claim 1 wherein the methylcellulose has a viscosity of >3000 centipoises.

7. The composition according to claim 1 wherein the methylcellulose is present in an amount of about 450 to about 550 mg.

8. The composition according to any of claim 1 or 2 to 7 wherein the lipase inhibitor is orlistat.

9. The composition according to any one of claim 1 or 2 to 8 compressed into a tablet.

10. A method for the dual treatment of adiposity and the faecal incontinence and steatorrhea associated therewith which method comprises administering to a mammal in need thereof a compressed tablet comprising:
   (a) at least one lipase inhibitor in an amount effective for treating adiposity; and
   (b) at least one water soluble, non-fermentable cellulose derivative having a viscosity of >1000 centipoise present in a sufficient amount to reduce the faecal incontinence and steatorrhea associated with coadministration of the lipase inhibitor; and
   (c) at least one excipient which is an edible calcium salt which is dibasic calcium phosphate dihydrate, calcium phosphate anhydrous, or tribasic calcium phosphate; or mixtures thereof.

11. The composition of claim 10 wherein the water soluble, non-fermentable cellulose derivative having a viscosity of >1000 centipoise is methylcellulose.

12. A pharmaceutical composition for a tablet comprising:
   (a) at least one water soluble, non-fermentable cellulose derivative which is methylcellulose having a viscosity of >1000 centipoise;
   (b) at least one lipase inhibitor in an amount effective for treating adiposity; and
   (c) at least one swellable diluent or filler, selected from the group consisting of microcrystalline cellulose, corn starch, or Starch 1500.

13. The composition according to claim 12 wherein the water soluble, non-fermentable cellulose derivative is methylcellulose having a viscosity of >2000 centipoise.

14. The composition according to claim 13 which further comprises a disintegrating agent.

15. The composition according to claim 14 which further comprises a wetting agent, and/or a lubricating agent.

16. The composition according to claim 15 which further comprises a binding agent.

17. The composition according to claim 12 wherein the diluent is microcrystalline cellulose and is present in a ratio of methylcellulose to microcrystalline cellulose from about 2.1 to about 14:1.

18. The composition according to claim 12 wherein the diluent is corn starch and is present in a ratio of methylcellulose to cornstarch of from about 7.5 to about 15:1.

19. A method for the dual treatment of adiposity and the faecal incontinence and steatorrhea associated therewith which method comprises administering to a mammal in need thereof a compressed tablet comprising:
   (a) at least one water soluble, non-fermentable cellulose derivative which is methylcellulose having a viscosity of >1000 centipoise;
   (b) at least one lipase inhibitor in an amount effective for treating adiposity; and
   (c) at least one swellable diluent or filler, selected from the group consisting of microcrystalline cellulose, corn starch, or Starch 1500.

20. A process for preparing a tablet formulation which process comprises:
   a) blending together to form an intragranular mixture high viscosity methylcellulose of >3000 cps; a diluent selected from the group consisting of microcrystalline cellulose, corn starch, or Starch 1500, or a mixture thereof, a lipase inhibitor, a lubricating agent and optionally a disintegrant; and
   b) adding to the mixture of step (a), a PVP aqueous solution, or alternatively spraying the mixture of step (a) with a PVP aqueous solution; and preparing granulates; and
   c) blending together an extragranular mixture of a wetting agent; a lubricating agent; a diluent; and a disintegrant, or a mixture thereof; and d) compacting the granulates of step (b) with the extra-granular mixture of step (c).

21. The process according to claim 20 wherein the admixture of the lipase inhibitor is added in step c) rather than step a).

22. A process for the manufacture of a pharmaceutical tablet, which process comprises mixing
   a) granulates comprising high viscosity methylcellulose of >3000 cps; at least one edible calcium salt which is dibasic calcium phosphate dihydrate, calcium phosphate anhydrous, or tribasic calcium phosphate; or mixtures thereof; a lipase inhibitor, and optionally together with an intra-granular disintegrant, and/or wetting agent, and/or colouring agent; with
   b) adding to the mixture of step (a), a PVP aqueous solution, or alternatively spraying the mixture of step (a) with a PVP aqueous solution; and preparing granulates; and
   c) blending together an extragranular mixture of a wetting agent; a lubricating agent; a diluent; and a disintegrant, or a mixture thereof; and
   d) compacting the granulates of step (b) with the extra-granular mixture of step (c).

23. The process according to claim 20 wherein the admixture of the lipase inhibitor is added in step c) rather than step a).

24. A pharmaceutical composition for an immediate release tablet comprising:
   (a) at least one lipase inhibitor in an amount effective for treating adiposity; (b) at least one water soluble, non-fermentable cellulose derivative which is methylcellulose having a viscosity of >1000 centipoise present in a sufficient amount to reduce the faecal incontinence and steatorrhea associated with coadministration of the lipase inhibitor; and
   (c) at least one excipient which is an edible calcium salt which is dibasic calcium phosphate dihydrate, calcium phosphate anhydrous, or tribasic calcium phosphate; or mixtures thereof.

* * * * *